United States Patent [19]
Gray et al.

[11] Patent Number: 5,097,495
[45] Date of Patent: Mar. 17, 1992

[54] COLLISION DETECTION CONTROL SYSTEM

[75] Inventors: Floyd L. Gray, Muskego; Duane A. Filtz, Brookfield; Christopher J. Gilling, Pewaukee, all of Wis.

[73] Assignee: General Electric Company, Milwaukee, Wis.

[21] Appl. No.: 676,609

[22] Filed: Mar. 28, 1991

[51] Int. Cl.$^5$ .............................................. H05G 1/54
[52] U.S. Cl. ........................................ 378/117; 378/91
[58] Field of Search ........................ 378/117, 91, 114

[56] References Cited

U.S. PATENT DOCUMENTS 4,733,408  3/1988  Beikuefner et al. ................. 378/117

OTHER PUBLICATIONS

Cross-Sectional View of Collision Sensor, admitted prior art.
GE Medical Systems, Advantx Card POS SP/BP Fluoro Schematics, Rev. B, Direction 19310, p. 24-2, admitted prior art.

Primary Examiner—Craig E. Church
Attorney, Agent, or Firm—Quarles & Brady

[57] ABSTRACT

An X-ray apparatus has a motor for moving its components in different directions. A collision sensor is formed by a bladder attached to a component of the apparatus and deformation of the bladder produces a change in the pressure of air within the bladder. The bladder has an air vent to the atmosphere which can be sealed by operation of a valve. A pressure sensor produces two control signals when the pressure within the bladder exceeds first and second threshold levels respectively. The second threshold level is greater in magnitude than said first threshold level. The first control signal closes the valve and causes a motor control circuit to discontinue any application of electricity to the motor. The second control signal opens a switch through which electricity normally flows to the motor. A mechanism also is provided to simulate a collision by compressing the bladder to test the operation of the detection system.

10 Claims, 2 Drawing Sheets

COLLISION DETECTION CONTROL SYSTEM

BACKGROUND OF THE INVENTION

The present invention relates to sensing systems for movable machines to detect when the machine has collided with an object, and particularly to such systems for motorized medical diagnostic equipment, such as X-ray machines.

In relatively large X-ray imaging systems, such as the one shown in U.S. Pat. No. 4,358,856, an X-ray source and a film holder are mounted on a movable gantry so that the components can be positioned at different angles with respect to the patient. For example, cardiac imaging often involves taking a series of X-ray images of a patient at various angles from the frontal projection through a plurality of oblique projections to a lateral projection, and through a plurality of head to foot angles in concert with the frontal and oblique projections. In order to position the gantry at each of the angles at which an exposure is to be taken, a series of motors move the gantry components with respect to the patient. The electrical drive circuitry for each motor is controlled by a set of switches operated by the X-ray technician.

Because the X-ray equipment is moving about a relatively immobile patient, a safeguard mechanism must be provided in the event of a collision between the moving equipment and the patient. In the past, sensor switches were mounted on various parts of the gantry which were likely to come into contact with the patient or the X-ray technician, during the operation of the equipment. In response to the sensor switches detecting a collision between the equipment and another object, the drive circuitry for the gantry motors was disabled until manually. A more advanced collision detection system automatically reversed the direction of the equipment when a collision was detected, until contact between the equipment and the object no longer was detected.

In power driven machines, it is important to provide a fail-safe mechanism which will sense when the machine has collided with an object or person and then stop the machine before any damage is done. Previous systems which merely sent a command to a motor control circuit when a collision was detected, did not provide such a mechanism as the collision could have been produced by a malfunction of that control circuit.

SUMMARY OF THE INVENTION

A system for detecting a collision between a device and an object has a deformable bladder attached to the device. The bladder includes an inner chamber that contains a fluid, such as air, at a predetermined pressure. Deformation of the bladder produces a change in the pressure of said fluid, which is detected by a means for sensing pressure changes. The pressure sensing means produces a first electrical signal when the bladder pressure exceeds a first threshold level. A passage is formed between the inner chamber and the external environment with a valve selectively sealing the passage in response to the first electrical signal.

The present invention has particular application as part of a motor control system in which the first electrical signal causes a motor controller to cease applying electricity to the motor. In such a system, the pressure sensing means also may produce a second electrical signal when the bladder pressure exceeds a second higher pressure threshold level. The second electrical signal opens a switch through which electricity normally flows to the motor. In this version, the switch provides a backup mechanism to stop the motor in the event that the motor controller fails to respond to the first electrical signal.

The preferred embodiment includes a mechanism which tests the operation of the collision detection system by compressing the bladder and insuring that the first and second electrical signals are produced.

An object of the present invention is to provide a system for detecting collisions between an apparatus and something else.

Another object is to provide such a mechanism which can stop motor driven components of the apparatus, such as those of an X-ray imaging system, in the event of a collision.

A further object of the present invention is to provide two mechanisms which respond to different degrees of contact with the apparatus. Should the first of these mechanisms fail, the second one provides an alternative apparatus to stop the motor driven component.

Yet another object is to provide a device for occasionally testing the operation of the collision detection system.

DETAILED DESCRIPTION OF THE INVENTION

Figure 1:
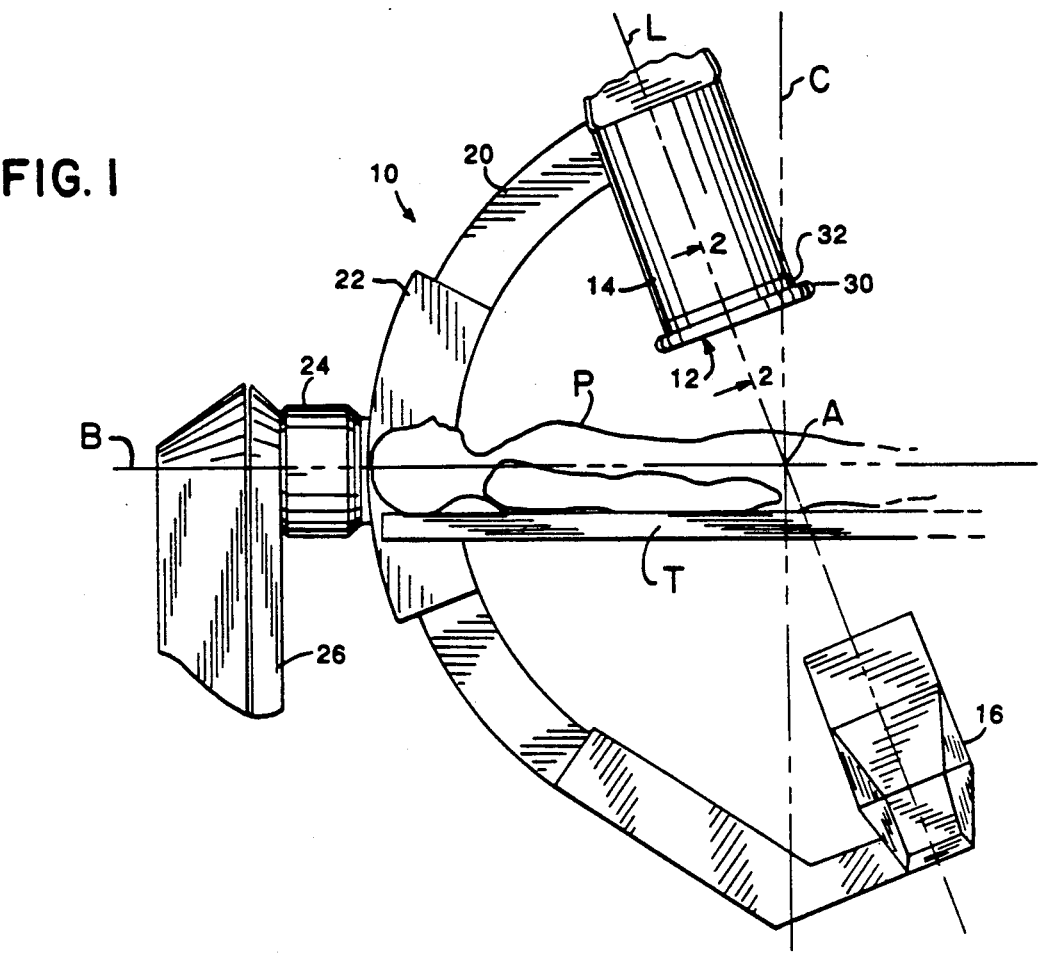
FIG. 1 is a side view of an X-ray system incorporating the present collision detection system.

With initial reference to FIG. 1, a medical diagnostic X-ray imaging apparatus 10 incorporates a collision sensor 12 according to the present invention. The imaging apparatus 10 has an X-ray source 16 and an image receiver 14, which includes an image intensifier and a cine camera, spaced apart from the source along a longitudinal axis L. The image receiver 14 and the X-ray source 16 are mounted at opposed ends of an arcuate arm 20 which rides in trackway 22 when driven by a motor that is hidden from view. The arm 20 can be driven in trackway 22 to rotate the image receiver 14 and X-ray source 16 in the plane of arm 20 about axis A, which as shown in FIG. 1 extends into the plane of the paper.

The image receiver 14 and X-ray source 16 may also be rotated about axis B, that extends through a bearing 24 connecting the trackway 22 to an upstanding leg 26. Leg 26, and therefore image receiver 14 and X-ray source 16, also are rotatable about a vertical axis C. All of the rotary motions about the three axes A, B and C are power driven by different electric motors mounted within the X-ray imaging apparatus 10. An X-ray imaging apparatus of this configuration is disclosed in commonly owned U.S. application Ser. No. 07/333,291 filed Apr. 4, 1989, which is incorporated herein by reference.

In operation, a patient P is supported on a table T between the image receiver 14 and the X-ray source 16 while the imaging apparatus 10 is driven to position the longitudinal axis L for production of an image in any desired plane through the patient. Since the receiver 14 is power driven in close proximity to the patient and to other equipment, the collision sensor 12 is provided to detect external contact with the image receiver 14. As can be seen in FIG. 1, the collision sensor 12 is located at the end of the image receiver 14 which is proximate to the patient P and which would be the most likely portion of the apparatus 10 to first contact a patient.

Figure 2:
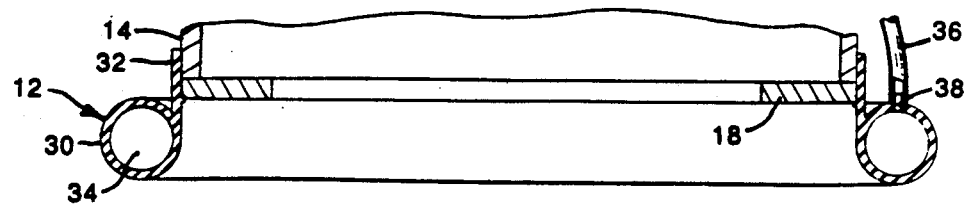
FIG. 2 is a cross section taken along line 2—2 through a portion of the system shown in FIG. 1 to illustrate a collision sensor.

FIG. 2 illustrates the details of the collision sensor 12 attached to the end of the image receiver 14. The collision sensor 12 has a toroidally shaped air bladder 30 and a circular flange 32 for mounting the air bladder 30 to the cylindrical housing of the image receiver 14. The collision sensor is formed of an elastic material which can be stretched around the periphery of the receiver to tightly hold the sensor in place. Additional fastening devices may be provided. The air bladder 30 of the collision sensor 32 forms a closed, collapsible, non-distensible chamber 34. The chamber 34 has a port 36 though the wall of the air bladder and a flexible tubing 38 is connected to the port in an air tight connection. As will be described, the tubing 38 couples the air bladder 30 to a pressure sensor.

Collisions with the receiver 14 also can result from objects entering the central opening of the air bladder 30 and striking an end plate 18 of the X-ray receiver 14 without striking the collision sensor 30. Such collisions can be detected by mounting a spring loaded, annular plate (not shown) on the end plate 18 and coupling switches to the annular plate which detect movement due to a collision. Such sensing plates have been used in previous X-ray apparatus and can be used in conjunction which the detection system of the present invention.

Figure 3:
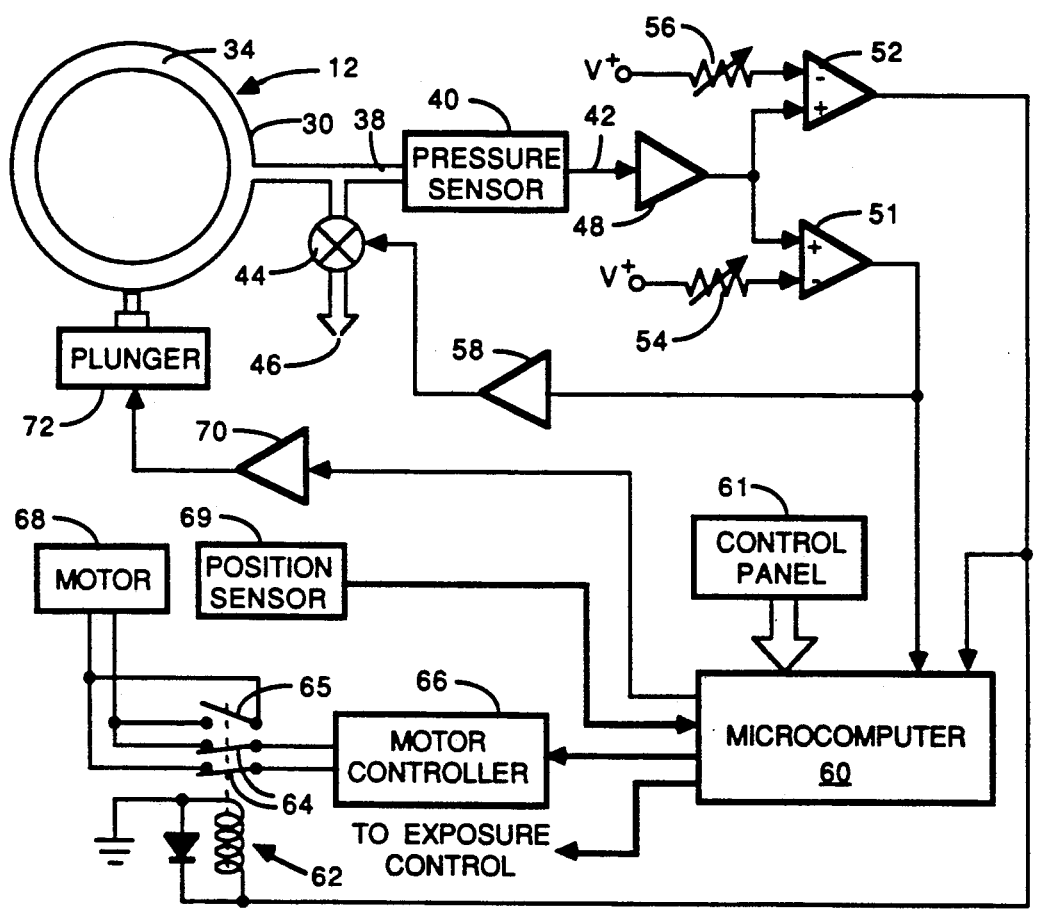
FIG. 3 is a schematic block diagram of a collision detection system.

FIG. 3 illustrates how the air bladder 30 is coupled to other components of the collision detection system. The tubing 38 is connected by a T fitting to an inlet of an electrically operated valve 44. The outlet of the valve 44 is connected to an orifice 46 having a smaller cross-sectional opening than the interior diameter of tubing 38. For example, the interior diameter of the tubing may be 0.750 inches whereas the diameter of the orifice is 0.005 inches. The significance of the relationship between these cross-sectional dimensions will be described hereinafter.

Tubing 38 also is connected to the input of a pressure sensor 40 that provides a voltage level on conductor 42 which corresponds in magnitude to the pressure within the bladder chamber 34. The output signal on conductor 42 from pressure sensor 40 is connected to the input of a operational amplifier 48. The amplified output signal from amplifier 48 is connected to the inputs of two differential amplifiers 51 and 52. The first differential amplifier 51 compares the voltage level representing the bladder pressure to a first pressure threshold as determined by a voltage applied to a second input of the first differential amplifier. The voltage level for the first pressure threshold is set by a first potentiometer 54. The output of the first differential amplifier 51, denoting the results of the comparison of the sensed bladder pressure to the first threshold, is applied by a valve driver 58 to the control input of the electrically operated valve 44. The output of the first differential amplifier 51 also is coupled to a digital input of a microcomputer 60.

The second differential amplifier 52 compares the voltage signal from the pressure sensor 40 to a voltage representing a second pressure threshold which is set by a second potentiometer 56. The second pressure threshold is greater in magnitude than the first threshold. The output of the second differential amplifier 52 is coupled to another digital input of the microcomputer 60 and to the coil of a fail safe relay 62. The relay 62 has two sets of normally closed contacts 64 and a set of normally open contacts 65 that are operated by the magnetic field produced by the relay coil, as will be described. The sets of normally closed contacts couple a motor controller 66 to a motor 68. The set of normally open contacts are connected across terminals of the motor 68.

The positioning of the image receiver 14 and the X-ray source 16 is controlled by the microcomputer 60. Such movement is initiated by the X-ray technician entering commands into a control panel 61 which applies signals to the microcomputer. These commands may either manually control the movement of the X-ray apparatus or commence an imaging sequence in which the X-ray source and receiver are automatically moved into a series of positions to acquire a number of images of the patient. For both types of commands, the microcomputer 60 responds by issuing control signals to the motor controller 66. The motor controller 66 in turn responds to the control signals by applying a d.c. voltage through relay contacts 64 to the motor 68 which signals have the proper polarity and magnitude to produce movement in the desired direction at a specified speed about one of the rotational axes A, B or C. Typically, the imaging apparatus 10 will have a separate motor to produce movement about each of the rotational axes. However, for simplicity of illustrating the present invention, only one such motor 68, controller 66 and fail safe relay 62 have been shown in FIG. 3.

The X-ray imaging apparatus 10 also includes a device 69 for detecting the angular position of its arm 20 and leg 26 about each of the rotational axes A, B and C and provide a signal indicative of that position to the microcomputer 60. The microcomputer uses such position information to determine when to stop the motor 68 and signal an X-ray exposure control system that the apparatus has been properly positioned for the acquisition of an image of the patient.

Under ideal operation, the image receiver 14 never comes into contact with the patient P and the collision detection system is never activated. During normal operation, valve 44 is open providing communication through orifice 46 between the chamber 34 of the air bladder 30 and the atmosphere. Therefore, the pressure within the bladder is at one atmosphere in this state.

Should a collision occur between the end of the image receiver 14 and the patient P or another object, the force of the collision will compress the air bladder 30 of the collision sensor 12. This compression increases the pressure within the chamber 34 which pressure increase is communicated by tube 38 to the pressure sensor 40. The pressure sensor 40 responds by producing a voltage on conductor 42 which indicates the rise in pressure. This pressure indicating signal is applied to both the first and second differential amplifiers 51 and 52 which compare the voltage level of the signal to the two respective threshold levels.

When the pressure increases above 0.5 inches of water, for example, the pressure exceeds the first threshold set by the first potentiometer 54. Upon this occurrence, the first differential amplifier 51 produces a positive output voltage, causing the driver 58 to close the electrically operated valve 44. It will be understood by those skilled in the art that because the orifice 46 at the valve output is extremely small in comparison to the inner diameter of the tube 38, the opening to the atmosphere provided by the orifice does not equalize the pressure fast enough to prevent the pressure sensor 40 from detecting the initial pressure increase due to a collision. The small orifice size allows a sufficient pressure rise to occur even during the slowest collision without impeding the ability of the air bladder to remain at atmospheric pressure under normal conditions. Once the valve closes the passage between the bladder 30 and the atmosphere, the pressure in chamber 34 can continue to rise with an increasing collision force.

The positive voltage level from the first differential amplifier 51 indicative of the pressure exceeding the first threshold also is received by the microcomputer 60. This voltage level causes the microcomputer to issue a control signal to the motor controller 66 and to similar controllers for other motors of the X-ray imaging apparatus 10. The control signal instructs the motor controller 66 to cease applying power to motor 68. In many instances, this action is sufficient to stop the movement of the X-ray imaging apparatus 10 before damage occurs to the patient or object struck by the image receiver 14.

If the apparatus 10 continues to move, further compression of the air bladder 30 will occur causing the pressure to rise above the second threshold. The second threshold, for example, is between four and seven inches of water as determined by the setting of the second potentiometer 56. When the pressure within the air bladder 30 rises above the second threshold, the signal from the pressure sensor 40 has a voltage in excess of the voltage provided at the input of the second differential amplifier 52 which is coupled to the second potentiometer 56.

This rise in the voltage of the pressure signal produces a positive output voltage from the second differential amplifier 52 which energizes the coil of relay 62. This action opens the normally closed contacts 64, disconnecting the motor 68 from its controller 66. Thus, relay 62 provides a redundant motor shut off mechanism which overrides any continued application of electricity to the motor 68 by the motor controller 66 should the latter device fail to respond to the control signals from the microcomputer 60 sent when the first pressure threshold was exceeded. In addition to opening the supply lines to the motor 68, the relay 62 also closes the normally open set of contacts to provide a dead short across the terminals of the motor 68, thus dynamically braking the motor.

After the collision detection circuit in FIG. 3 has responded to the pressure rising above the second threshold, the X-ray technician must take manual steps in order to remove the collision condition. This may require the X-ray technician to manually move to the imaging apparatus 10 away from the struck object. After contact with the sensor 12 has been removed and the pressure within the bladder 30 drops below the first threshold, the signal from the first differential amplifier 51 will go false providing an indication to the microcomputer 60 of the removal of the collision condition. This signal also causes the valve driver 58 to open the electrically operated valve 44, once again venting the air bladder chamber 34 to the atmosphere, thereby equalizing the pressure. The technician also may enter a command into control panel 61 to reverse the motor direction, while a first level collision is detected, to move the apparatus a small distance.

Alternatively, after the motor 68 has stopped in response to the pressure initially exceeding the first threshold, the microcomputer 60 automatically may issue another control signal to the motor controller 66, thereby causing the motor 68 to move the component of the X-ray system 10 in the opposite direction to that in which it was going at the time of the collision.

The proper operation of the collision detection system is critical for safety of the patient being examined. Therefore, the present control system shown in FIG. 3 provides a mechanism by which the performance of the collision detection system is occasionally tested to insure satisfactory operation. A digital output of the microcomputer 60 is coupled by a driver amplifier 70 to an electromechanical plunger 72. The plunger, when activated by a signal from the microcomputer, presses against the air bladder 30 compressing the bladder and increasing the pressure within chamber 34 to simulate a collision. Such a testing can follow the occurrence of any one of several events, such as power up or resetting of the X-ray system, clearing any collision, or at periodic time intervals when an examination is not in progress. The performance of a test following these events is included in a motor control program of the microcomputer 60.

The test is performed by the microcomputer 60, sending a control signal through the driver amplifier 70 to activate the plunger 72. When activated, the plunger slowly compresses the air bladder 30 to produce a rise in the pressure. The microcomputer then examines the input signals from the first and second differential amplifiers 51 and 52 to insure that both signals occur in the proper sequence. Such testing will detect a puncture of the air bladder 30 or tubing 38, as well as a malfunction in the sensing system or valve 44. During this testing process the microcomputer can attempt to move the motor thus checking the action of the fail safe relay 62. If a malfunction is detected, the microcomputer 60 provides a signal to the technician and if desired, disables further automatic movement of the X-ray imaging apparatus 10.

We claim:

1. In an X-ray apparatus having a structural member driven by a motor, a motor control circuit comprising:
   a deformable bladder attached to the structural member and having a chamber that contains a fluid at a pressure, and deformation of said bladder producing a change in the pressure of the fluid;
   a passage between the chamber and the environment of said bladder;
   means for sensing pressure changes in said bladder and producing an output signal having a voltage level indicative of the pressure;
   means for producing a first control signal when the voltage level of the output signal exceeds a first threshold level;
   means for producing a second control signal when the voltage level of the output signal exceeds a second threshold level;
   a valve for sealing said passage in response to the first control signal;
   a motor controller for selectively applying electricity to the motor and which discontinues any application of electricity to the motor in response to the first control signal; and
   a first switch means coupled between the motor and said motor controller and through which the electricity flows to the motor, said switch opening in response to said second control signal.

2. The motor control circuit as recited in claim 1 wherein:

said means for producing a first control signal comprises a first means for comparing the the voltage level of the output signal to a first reference voltage level; and said means for producing a second control signal comprises a first means for comparing the the voltage level of the output signal to a second reference voltage level.

3. The motor control circuit as recited in claim 1 further comprising further comprising a normally open second switch means coupled across terminals of the motor and closing in response to said second control signal.

4. The motor control circuit as recited in claim 1 further comprising a testing means for compressing said bladder; and a means for detecting production of the first and second control signals when said testing means compresses said bladder.

5. The motor control circuit as recited in claim 1 where the second threshold level is greater in magnitude than said first threshold level.

6. In an X-ray apparatus having a structural member driven by a motor, a motor control circuit comprising:
a deformable bladder attached to the structural member and having a chamber that contains a fluid at a pressure, and deformation of said bladder producing a change in the pressure of the fluid;
a passage between the chamber and the external environment of said bladder;
means for sensing pressure changes in said bladder and producing a first electrical signal indicating when the pressure exceeds a first threshold level;
a motor controller for applying electricity to the motor and which discontinues any application of electricity to the motor in response to the first electrical signal; and
a valve for selectively sealing said passage in response to the first electrical signal.

7. The motor control circuit as recited in claim 6 wherein said means for sensing pressure changes produces a second electrical signal indicating when the pressure exceeds a second threshold level which is greater in magnitude than said first threshold level; and
further comprising a first switch coupled between the motor and said motor controller and through which electricity flows to the motor, said first switch opening in response to the second electrical signal.

8. The motor control circuit as recited in claim 7 further comprising a normally open second switch coupled across terminals of the motor and closing in response to the second electrical signal.

9. The motor control circuit as recited in claim 6 further comprising a testing means for compressing said bladder; and a means for detecting production of the first electrical signal when said testing means compresses said bladder.

10. The motor control circuit as recited in claim 6 wherein said means for sensing pressure changes produces a second electrical signal indicating when the pressure exceeds a second threshold level; and
further comprising a testing means for compressing said bladder and detecting production of the first and second electrical signals when said bladder is compressed by said testing means.

* * * * *